United States Patent
Okamoto et al.

(10) Patent No.: US 9,796,655 B2
(45) Date of Patent: Oct. 24, 2017

(54) METHOD FOR PRODUCING CARBONATE COMPOUND

(71) Applicant: Asahi Glass Company, Limited, Tokyo (JP)

(72) Inventors: Hidekazu Okamoto, Tokyo (JP); Atsushi Fujimori, Tokyo (JP); Takashi Okazoe, Tokyo (JP)

(73) Assignee: ASAHI GLASS COMPANY, LIMITED, Tokyo (JP)

(*) Notice: Subject to any disclaimer, the term of this patent is extended or adjusted under 35 U.S.C. 154(b) by 169 days.

(21) Appl. No.: 14/730,432

(22) Filed: Jun. 4, 2015

(65) Prior Publication Data

US 2015/0284314 A1 Oct. 8, 2015

Related U.S. Application Data

(63) Continuation of application No. PCT/JP2013/082584, filed on Dec. 4, 2013.

(30) Foreign Application Priority Data

Dec. 6, 2012 (JP) ................. 2012-267084

(51) Int. Cl.
*C07C 68/00* (2006.01)

(52) U.S. Cl.
CPC .................... *C07C 68/00* (2013.01)

(58) Field of Classification Search
None
See application file for complete search history.

(56) References Cited

U.S. PATENT DOCUMENTS

| 4,353,831 A | 10/1982 | Strege et al. |
| 2010/0240912 A1 | 9/2010 | Okamoto et al. |
| 2010/0249436 A1 | 9/2010 | Okamoto et al. |

FOREIGN PATENT DOCUMENTS

| JP | S60-197639 A | 10/1985 |
| JP | H07-206847 A | 8/1995 |
| RU | 2 309 935 C1 | 11/2007 |
| WO | WO 2009/072501 A1 | 6/2009 |
| WO | WO 2009/072502 A1 | 6/2009 |
| WO | WO 2010/140572 A1 | 12/2010 |

OTHER PUBLICATIONS

R. Srivastava et al., Fe—Zn Double Metal Cyanide Complexes as Novel, Solid Transesterification Catalysts, Journal of Catalysis, 241, 2006, pp. 34-44.
International Search Report dated Feb. 17, 2014 issued in Application No. PCT/JP2013/082584.
The Extended European Search Report issued in Application No. 13860942.5 dated Jun. 17, 2016.

*Primary Examiner* — Kamal Saeed
(74) *Attorney, Agent, or Firm* — Foley & Lardner LLP

(57) ABSTRACT

The present invention relates to a production process capable of selectively producing various kinds of carbonate compounds without restraint in high yields without using toxic compounds such as phosgene and crown ethers, without producing corrosive gases such as hydrogen chloride as a by-product, and without necessity of removing the chloroform as a by-product by distillation, and to a method for producing a carbonate compound, containing reacting compound (1) with a compound having an OH group in the presence of a metal salt and 0.2 to 4.0 mol of compound (2) per mol of the metal salt to obtain a carbonate compound, in which m is an integer of 1-10, Q is an alkylene group having 1 to 4 carbon atoms, etc., and $R^{10}$ and $R^{11}$ are alkyl groups having 1 to 5 carbon atoms, etc.

[Chem. 1]

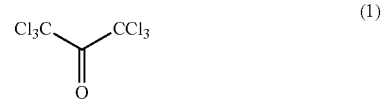

(1)

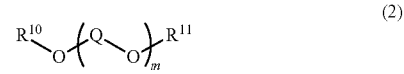

(2)

9 Claims, No Drawings

METHOD FOR PRODUCING CARBONATE COMPOUND

CROSS REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/082584 filed on Dec. 4, 2013, which is based upon and claims the benefit of priority of Japanese Application No. 2012-267084 filed on Dec. 6, 2012, the entire contents of which are hereby incorporated by reference in their entireties.

TECHNICAL FIELD

The present invention relates to a method for producing a carbonate compound.

BACKGROUND ART

As processes for producing a carbonate compound which does not use phosgene having toxicity, the following processes are known.

(1) A process for producing a cyclic carbonate by reacting carbon dioxide gas with an alkene oxide in the presence of a catalyst (see, e.g., Patent Document 1).

(2) A process for producing by an ester exchange reaction of a cyclic carbonate or dimethyl carbonate with an alcohol in the presence of an ester exchange reaction catalyst (see, e.g., Non-Patent Document 1).

(3) A process for producing by reacting methyl chloroformate with an alcohol (see, e.g., Patent Document 2).

(4) A process for producing by reacting hexachloroacetone with an alcohol.

However, the process (1) involves problems that only cyclic carbonates can be produced and various carbonates cannot be selectively produced.

The process (2) involves problems that since it is an equilibrium reaction, a large excess of an alcohol should be used for improving the yield of the objective product; that it is difficult to separate and remove an asymmetrical carbonate compound produced as a by-product; and the like.

The process (3) involves problems that production facilities are corroded with hydrogen chloride produced as a by-product; and the like.

As the process (4), for example, the following processes have been disclosed.

(4-1) A process of reacting a vicinal diol compound (propylene glycol, etc.) with hexachloroacetone in the presence of a base catalyst (a salt of a strong base with a weak acid) to obtain a cyclic alkylene carbonate and chloroform (Patent Document 3).

(4-2) A process of reacting a vicinal diol compound (propylene glycol, etc.) with hexachloroacetone in the presence of a Group 2 or 3 metal hydrosilicate catalyst to obtain a cyclic alkylene carbonate and chloroform (Patent Document 4).

(4-3) A process of reacting hexachloroacetone with a compound having an OH group in the presence of a halogen salt catalyst to obtain a compound having a carbonate bond (Patent Document 5).

(4-4) A process of reacting hexachloroacetone with a fluorine-containing compound having an OH group to obtain a fluorine-containing compound having a carbonate bond (Patent Document 6).

In the processes (4-1) and (4-2), a cyclic carbonate compound has been obtained by the reaction of hexachloroacetone with a vicinal diol compound in the presence of a catalyst. However, according to the investigation made by the present inventors, it is expected that the direct application to the reactions of hexachloroacetone with other diols and monools may be difficult because the reaction rate of the carbonate formation reaction by intramolecular cyclization is very high in the case of a diol compound having adjacent OH groups in a vicinal position.

Moreover, in the processes (4-1) and (4-2), chloroform (non-polar solvent) formed by the reaction of hexachloroacetone with the vicinal diol compound decreases the solubility of the catalyst in the substrates to lower the yield of the objective compound, so that it is necessary to remove the chloroform by distillation during the reaction of hexachloroacetone with the vicinal diol compound. However, in order to remove the chloroform by distillation simultaneously with the reaction, a dedicated facility becomes necessary, which is industrially disadvantageous.

Further, in the process (4-1), it is described that a crown ether is effective as a phase transfer catalyst and a non-cyclic glycol ether or another ether can be used as an inert solvent. However, a crown ether has toxicity and is expensive, which are industrially disadvantageous. Also, in the case of using a solvent, it is necessary to separate the solvent from the reaction mixture after the reaction, which is industrially disadvantageous.

Also in the processes (4-3) and (4-4), for the aforementioned reason, it is necessary to remove chloroform by distillation during the reaction of hexachloroacetone with the compound having an OH group. However, the case of removing the chloroform by distillation involves the following problems.

In order to remove the chloroform by distillation simultaneously with the reaction, a dedicated facility becomes necessary, which is industrially disadvantageous.

In the case where the compound having an OH group forms an azeotrope with chloroform, the compound having an OH group as a raw material is also distilled away.

CITATION LIST

Patent Document

Patent Document 1: JP-A-H07-206847
Patent Document 2: JP-A-S60-197639
Patent Document 3: U.S. Pat. No. 4,353,831
Patent Document 4: Russian Patent No. 2309935
Patent Document 5: WO2009/072501
Patent Document 6: WO2009/072502

Non-Patent Document

Non-Patent Document 1: Journal of Catalysis, 2006, Vol. 241, No. 1, p. 34-44

SUMMARY OF THE INVENTION

Problem that the Invention is to Solve

The present invention provides a novel production process capable of selectively producing various kinds of carbonate compounds without restraint in high yields without using toxic compounds such as phosgene and a crown ether, without producing corrosive gases such as hydrogen chloride as a by-product, and without necessity of removing the chloroform as a by-product by distillation.

Means for Solving the Problem

The method for producing a carbonate compound according to the present invention is a process containing reacting a compound represented by the following formula (1) with a compound having an OH group in the presence of a metal salt and 0.2 to 4.0 mol of a compound represented by the following formula (2) per mol of the metal salt to obtain a compound having a carbonate bond.

[Chem. 1]

(1)

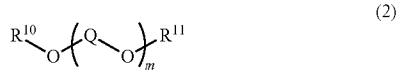
(2)

Here, m is an integer of from 1 to 10; Q is an alkylene group having 1 to 4 carbon atoms or a group in which one or more hydrogen atoms of the alkylene group are replaced by an alkyl group having 1 to 5 carbon atoms or by an alkyl group having 2 to 5 carbon atoms and having an ethereal oxygen atom between carbon atom-carbon atom, and Q in the case where m is 2 or more may be the same group or a different group; and $R^{10}$ and $R^{11}$ are each independently an alkyl group having 1 to 5 carbon atoms.

In the method for producing a carbonate compound according to the present invention, it is preferred that chloroform produced by the reaction is not removed by distillation during the reaction of the compound represented by the formula (1) with the compound having an OH group.

The metal salt is preferably at least one kind selected from the group consisting of salts of alkali metals and salts of alkaline earth metals.

The compound represented by the above formula (2) is preferably a compound represented by the following formula (21).

[Chem. 2]

(21)

Here, m is an integer from 2 to 6, and $R^{10}$ and $R^{11}$ are each independently an alkyl group having 1 to 5 carbon atoms.

The compound having a carbonate bond is preferably a compound represented by the following formula (31) or a compound represented by the following formula (32).

[Chem. 3]

(31)

-continued

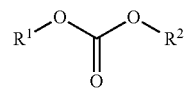
(32)

Here, $R^1$ and $R^2$ represent each a monovalent aliphatic hydrocarbon group and $R^1$ and $R^2$ are not the same group.

The compound having a carbonate bond is also preferably a cyclic carbonate compound represented by the following formula (3a), or a chainlike carbonate compound represented by the following formula (3b).

[Chem. 4]

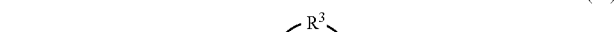
(3a)

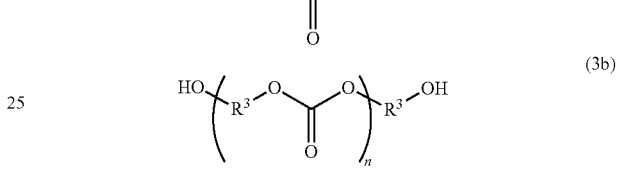
(3b)

Here, $R^3$ represents a divalent aliphatic hydrocarbon group and n represents an integer of from 1 to 1,000.

The compound having an OH group in the case of a compound having one OH group is preferably at least one selected from the group consisting of methanol, ethanol, 1-propanol, 2-propanol, 1-butanol, tert-butyl alcohol, 3-oxa-1-butanol, 2,2,2-trifluoroethanol, 2,2,3,3,3-pentafluoropropanol, 2,2,3,3-tetrafluoropropanol, 1-trifluoromethyl-2,2,2-trifluoro-1-ethanol, 2,2,3,4,4,4-hexafluorobutanol, 2,2,3,3,4,4,5,5-octafluoropentanol, 2,2-difluoro-2-(1,1,2,2-tetrafluoro-2-(pentafluoroethoxy)ethoxy)ethanol, 2,2-difluoro-2-(tetrafluoro-2-(tetrafluoro-2-(pentafluoroethoxy)ethoxy)ethoxy)ethanol, 2,3,3,3-tetrafluoro-2-(1,1,2,3,3,3-hexafluoro-2-(1,1,2,2,3,3,3-heptafluoropropoxyl)propoxy)-1-propanol, and 2,3,3,3-tetrafluoro-2-(1,1,2,2,3,3,3-heptafluoropropoxy)-1-propanol, and is more preferably at least one kind selected from the group consisting of methanol, ethanol, 1-propanol, 2-propanol, 2,2,2-trifluoroethanol, 2,2,3,3,3-pentafluoropropanol, 2,2,3,3-tetrafluoropropanol, and 1-trifluoromethyl-2,2,2-trifluoro-1-ethanol.

The compound having an OH group in the case of a compound having two OH group is preferably at least one kind selected from the group consisting of ethylene glycol, 1,2-propylene glycol, 3-methyl-1,5-pentanediol, 3-oxa-1,5-pentanediol, 1,6-hexanediol, 1,3-propanediol, 1,2-butanediol, and 1,4-butanediol.

Advantageous Effect of the Invention

According to the process for producing a carbonate compound of the present invention, various kinds of carbonate compounds can be selectively produced without restraint in high yields without using toxic compounds such as phosgene and a crown ether, without producing corrosive gases such as hydrogen chloride as a by-product, and without necessity of removing the chloroform as a by-product by distillation. Moreover, in addition to cyclic carbonates, oligomers or polymers of carbonates having a reactive functional group at the terminal can be easily produced.

MODE FOR CARRYING OUT THE INVENTION

In the present specification, the compound represented by the formula (1) is referred to as compound (1). The compounds represented by the other formulae are also similarly referred to.

<Carbonate Compounds>

The carbonate compounds obtained by the production process of the present invention are compounds having a carbonate bond [—O—C(=O)—O—].

The carbonate compounds include compound (31), compound (32), compound (3a), compound (3b), and branched carbonate compounds having more than two terminal OH groups (hereinafter referred to as branched carbonate compounds).

[Chem. 5]

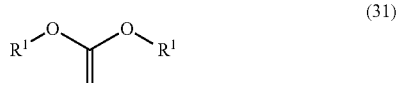

(31)

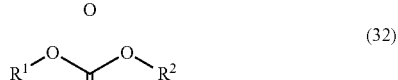

(32)

(3a)

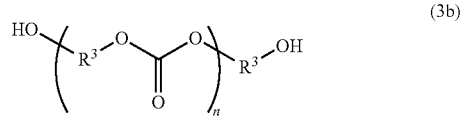

(3b)

(Compound (31))

$R^1$ represents a monovalent aliphatic hydrocarbon group. $R^1$'s on the left and right sides are the same group.

The monovalent aliphatic hydrocarbon group may have an ethereal oxygen atom.

The monovalent aliphatic hydrocarbon group may be linear, branched, or cyclic.

$R^1$ may have a substituent. The substituent is preferably a halogen atom in view of usefulness of the compound (31).

The monovalent aliphatic hydrocarbon group is preferably an aliphatic hydrocarbon group having 1 to 9 carbon atoms and more preferably an aliphatic hydrocarbon group having 1 to 6 carbon atoms. In view of usefulness of the compound (31), at least one selected from methyl group, ethyl group, n-propyl group, iso-propyl group, n-butyl group, tert-butyl group, 3-oxa-n-butyl group, 2,2,2-trifluoroethyl group, 2,2,3,3,3-pentafluoropropyl group, 2,2,3,3-tetrafluoropropyl group, 1-trifluoromethyl-2,2,2-trifluoroethyl group, 2,2,3,4,4,4-hexafluorobutyl group, 2,2,3,3,4,4,5,5-octafluoropentyl group, 2,2-difluoro-2-(1,1,2,2-tetrafluoro-2-(pentafluoroethoxy)ethoxy)ethyl group, 2,2-difluoro-2-(tetrafluoro-2-(tetrafluoro-2-(pentafluoroethoxy)ethoxy)ethoxy)ethyl group, 2,3,3,3-tetrafluoro-2-(1,1,2,3,3,3-hexafluoro-2-(1,1,2,2,3,3,3-heptafluoropropoxy)propoxy) propyl group, and 2,3,3,3-tetrafluoro-2-(1,1,2,2,3,3,3-heptafluoropropoxyl)propyl group is more preferred.

(Compound (32))

$R^1$ and $R^2$ represent each a monovalent aliphatic hydrocarbon group. $R^1$ and $R^2$ are not the same group.

The monovalent aliphatic hydrocarbon group may have an ethereal oxygen atom.

The monovalent aliphatic hydrocarbon group may be linear, branched, or cyclic.

$R^1$ and $R^2$ may have a substituent. The substituent is preferably a halogen atom in view of usefulness of the compound (32).

The monovalent aliphatic hydrocarbon group is preferably an aliphatic hydrocarbon group having 1 to 9 carbon atoms and more preferably an aliphatic hydrocarbon group having 1 to 6 carbon atoms. In view of usefulness of the compound (32), at least one selected from methyl group, ethyl group, n-propyl group, iso-propyl group, n-butyl group, tert-butyl group, 3-oxa-n-butyl group, 2,2,2-trifluoroethyl group, 2,2,3,3,3-pentafluoropropyl group, 2,2,3,3-tetrafluoropropyl group, 1-trifluoromethyl-2,2,2-trifluoroethyl group, 2,2,3,4,4,4-hexafluorobutyl group, 2,2,3,3,4,4,5,5-octafluoropentyl group, 2,2-difluoro-2-(1,1,2,2-tetrafluoro-2-(pentafluoroethoxy)ethoxy)ethyl group, 2,2-difluoro-2-(tetrafluoro-2-(tetrafluoro-2-(pentafluoroethoxy)ethoxy)ethoxy)ethyl group, 2,3,3,3-tetrafluoro-2-(1,1,2,3,3,3-hexafluoro-2-(1,1,2,2,3,3,3-heptafluoropropoxy)propoxy) propyl group, and 2,3,3,3-tetrafluoro-2-(1,1,2,2,3,3,3-heptafluoropropoxyl)propyl group is more preferred.

The asymmetrical compound (32) is known to have a melting point lower than that of the symmetrical compound (31) and is predicted to be superior in the case where it is used as a solvent or the like.

(Compound (3a))

The compound (3a) is a cyclic carbonate compound.

$R^3$ represents a divalent aliphatic hydrocarbon group.

The divalent aliphatic hydrocarbon group may have an ethereal oxygen atom.

The divalent aliphatic hydrocarbon group may be linear, branched, or cyclic.

$R^3$ may have a substituent. The substituent is preferably a halogen atom in view of usefulness of the compound (3a).

$R^3$ is preferably an aliphatic hydrocarbon group having 1 to 15 carbon atoms and, in view of usefulness of the compound (3a), more preferably —CH$_2$CH$_2$—, —CH$_2$CH(CH$_3$)—, —CH$_2$CH(C$_2$H$_5$)—, or —CH$_2$CH$_2$CH$_2$—.

The compound (3a) is preferably ethylene carbonate, 1,2-propylene carbonate, 1,3-propylene carbonate, or 1,2-butylene carbonate.

(Compound (3b))

The compound (3b) is an oligomer or polymer having OH groups that is a reactive group at the terminal.

$R^3$ represents a divalent aliphatic hydrocarbon group. In the case where a plurality of $R^3$'s are present in the compound (3b), $R^3$'s may be a single kind or may be two or more kinds.

The divalent aliphatic hydrocarbon group may have an ethereal oxygen atom.

The divalent aliphatic hydrocarbon group may be linear, branched, or cyclic.

$R^3$ may have a substituent. The substituent is preferably a halogen atom in view of usefulness of the compound (3b).

$R^3$ is preferably an aliphatic hydrocarbon group having 1 to 15 carbon atoms, which may have an ethereal oxygen atom and, in view of usefulness of the compound (3b), more preferably —CH$_2$CH$_2$CH(CH$_3$)CH$_2$CH$_2$—, —CH$_2$CH$_2$CH$_2$CH$_2$CH$_2$CH$_2$—, —CH$_2$CH$_2$CH$_2$CH$_2$—, —CH₂CH₂CH₂—, —CH₂CH₂(OCH₂CH₂)ₓ— (where x is an integer of from 1 to 4), dipropylene glycol, or tripropylene glycol.

n represents an integer of from 1 to 1,000 and is preferably an integer of from 5 to 100 and more preferably an integer of from 10 to 50. Incidentally, as the reaction product, the compound (3b) is usually obtained as a mixture of compounds having different n numbers.

The compound (3b) includes poly(1,3-propylene carbonate), poly(1,4-butylene carbonate), poly(3-methyl-1,5-pentylene carbonate), poly(3-oxa-1,5-pentylene carbonate), poly(1,6-hexylene carbonate), —(CH₂CH₂OCH₂CH₂—O—(CO)—O)ₙ—, —(CH₂CH₂OCH₂CH₂OCH₂CH₂—O—(CO)—O)ₙ—, —(CH₂CH₂OCH₂CH₂OCH₂CH₂OCH₂CH₂—O—(CO)—O)ₙ—, —((CH(CH₃)CH₂O)ₓ—(CO)—O)ₙ— (where z is 2 or 3), and copolymers having these repeating units.

(Branched Carbonate Compound)

The branched carbonate compound includes branched oligomers and branched polymers, each having more than two terminal OH groups. Here, the branched carbonate compound having more than two terminal OH groups includes those each having three or more terminal OH groups and mixtures of those each having two terminal OH groups and those each having three or more terminal OH groups. In the case of the mixtures, "more than two" indicates an average value, for example, 2.05, 2.1, or the like.

<Process for Producing Carbonate Compound>

The method for producing a carbonate compound of the present invention is a process for obtaining a carbonate compound by reacting the compound (1) with a compound having an OH group in the presence of a metal salt and the compound (2).

[Chem. 6]

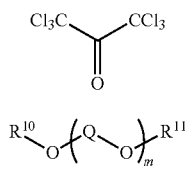

(1)

(2)

(Compound (1))

The compound (1) is hexachloroacetone.

Hexachloroacetone can be produced by the processes of chlorinating acetone as described in JP-B-S60-52741 and JP-B-S61-16255.

(Compound (2))

The compound (2) can improve the affinity of the metal salt that is a catalyst with the compound (1) that is a raw material, the compound having an OH group and chloroform as a by-product; and also can promotes the reaction of the compound (1) with the compound having an OH group by increasing the degree of dissociation of the metal salt in the compound having an OH group and chloroform. Particularly, it has a remarkable reaction-promoting effect in an aprotic solvent such as chloroform as a by-product and hence exhibits a large effect in the later stage of the reaction where the concentration of the compound having an OH group as a raw material decreases and the concentration of chloroform as a by-product increases.

m is an integer from 1 to 10.

m varies depending on the kind of the metal salt used but, from the standpoint of effective coordinating ability, is an integer of preferably from 1 to 6, more preferably from 2 to 5, and further preferably from 2 to 4.

Q is an alkylene group having 1 to 4 carbon atoms or a group in which one or more hydrogen atoms of the alkylene group are replaced with an alkyl group having 1 to 5 alkyl group or by an alkyl group having 2 to 5 carbon atoms and having an ethereal oxygen atom between carbon atom-carbon atom.

Q in the case where m is 2 or more may be the same group or a different group.

From the standpoints of steric hindrance at the time of including the metal salt through coordination by the oxygen atom and industrial versatility, Q is preferably a linear alkylene group, more preferably a linear alkylene group having 1 to 4 carbon atoms, and particularly preferably —CH₂CH₂—.

$R^{10}$ and $R^{11}$ are each independently an alkyl group having 1 to 5 carbon atoms.

From the standpoints of steric hindrance at the time of including the metal salt through coordination by the oxygen atom and industrial versatility, similarly, $R^{10}$ and $R^{11}$ are preferably methyl group or ethyl group, and particularly preferably methyl group.

The compounds (2) in which Q is —CH₂CH₂— in the formula (2) include 1,2-dimethoxyethane [m=1, monoglyme], diglyme [m=2], triglyme [m=3], tetraglyme [m=4], pentaglyme [m=5], hexaglyme [m=6], 1,2-diethoxyethane, diethylene glycol-diethyl ether, diethylene glycol-di-n-propyl ether, diethylene glycol-di-iso-propyl ether, diethylene glycol-di-n-butyl ether, triethylene glycol-diethyl ether, triethylene glycol-di-n-propyl ether, triethylene glycol-di-iso-propyl ether, triethylene glycol-di-n-butyl ether, tetraethylene glycol-diethyl ether, tetraethylene glycol-di-n-propyl ether, tetraethylene glycol-di-iso-propyl ether, tetraethylene glycol-di-n-butyl ether, pentaethylene glycol-diethyl ether, pentaethylene glycol-di-n-propyl ether, pentaethylene glycol-di-iso-propyl ether, pentaethylene glycol-di-n-butyl ether, hexaethylene glycol-diethyl ether, hexaethylene glycol-di-n-propyl ether, hexaethylene glycol-di-iso-propyl ether, hexaethylene glycol-di-n-butyl ether, and the like.

The compounds in which $R^{10}$ and $R^{11}$ are methyl group or ethyl group and m is an integer of 2 to 4 including the case where Q is a group other than —CH₂CH₂— in the formula (2) include compounds represented by the following formulae, provided that Et represents ethyl group.

[Chem. 7]

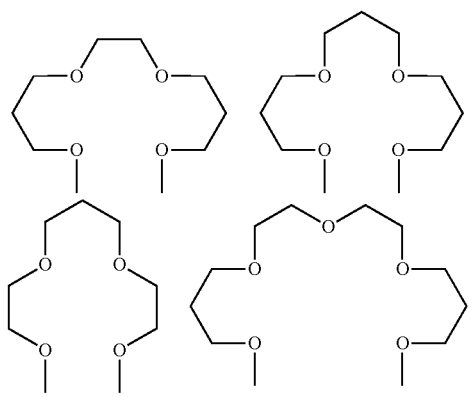

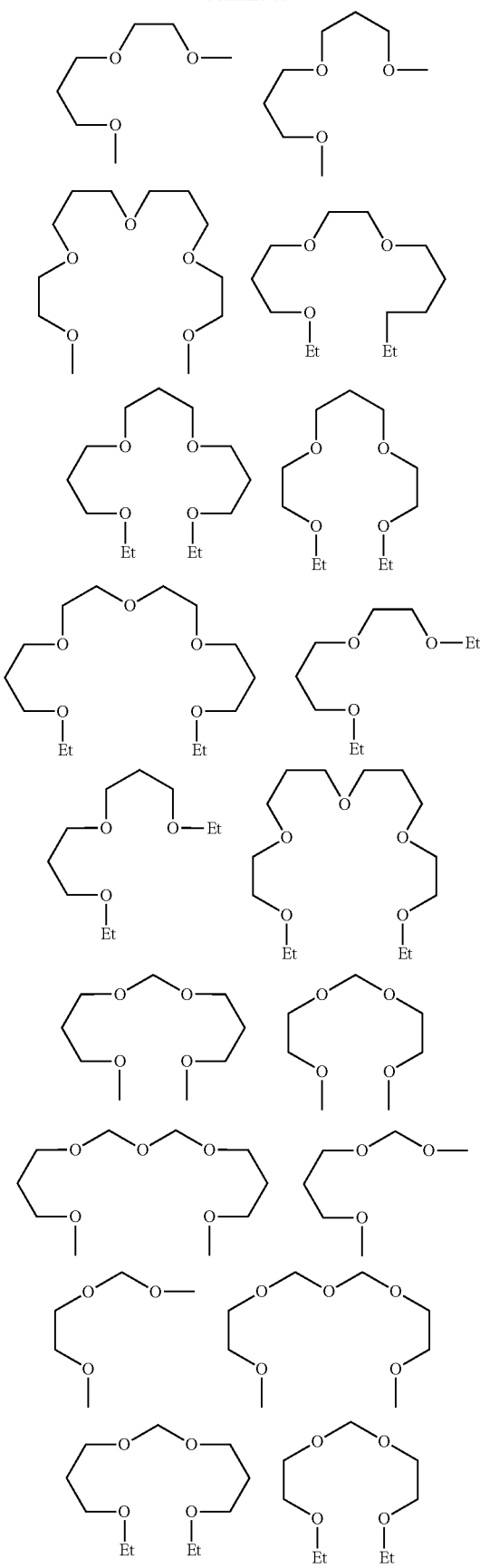

-continued

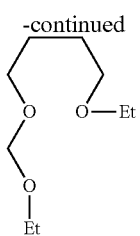

From the standpoints of steric hindrance at the time of including the metal salt through coordination by the oxygen atom and industrial versatility, the compound (2) is preferably compound (21).

[Chem. 9]

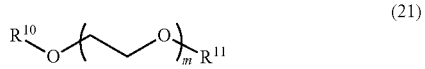

The compound (21) is preferably monoglyme, diglyme, triglyme, tetraglyme, pentaglyme, hexaglyme, diethylene glycol diethyl ether, triethylene glycol diethyl ether, tetraethylene glycol diethyl ether, pentaethylene glycol diethyl ether, or hexaethylene glycol diethyl ether and is more preferably monoglyme, diglyme, triglyme, tetraglyme, pentaglyme, or hexaglyme.

The amount of the compound (2) is from 0.2 to 4.0 mol, preferably from 0.5 to 4.0 mol, and more preferably from 1.0 to 3.0 mol, per mol of the metal salt. In the case where the amount of the compound (2) is small, the amount of the coordination to the metal becomes insufficient and hence the reaction-promoting effect decreases. In the case where the amount of the compound (2) is too large, the separation of the metal salt becomes difficult and there is caused a decrease in distillation yields in the distillation for purification after the reaction.

(Metal Salt)

By using the metal salt as a catalyst, the reaction of the compound (1) with the compound having an OH group can be efficiently carried out and the yields can be improved.

From the standpoints of high catalyst activity and industrial versatility, the metal salt is preferably one or more selected from the group consisting of salts of alkali metals and salts of alkaline earth metals.

The alkali metals include Li, Na, K, Rb, Cs, and the like.
The alkaline earth metals includes Be, Ca, Sr, and the like.
The salts of the alkali metals and alkaline earth metals include halogen salts, carbonate salts, hydroxides, alkoxides, and the like.

The halogen salts of the alkali metals include LiF, LiCl, LiBr, LiI, NaF, NaCl, NaBr, NaI, KF, KCl, KBr, KI, RbF, RbCl, RbBr, RbI, CsF, CsCl, CsBr, CsI, and the like.

The halogen salts of the alkaline earth metals include $BeF_2$, $BeCl_2$, $BeBr_2$, $BeI_2$, $CaF_2$, $CaCl_2$, $CaBr_2$, $CaI_2$, $SrF_2$, $SrCl_2$, $SrBr_2$, and $SrI_2$.

The carbonate salts of the alkali metals include $Li_2CO_3$, $Na_2CO_3$, $K_2CO_3$, $Rb_2CO_3$, $Cs_2CO_3$, and the like.

The carbonate salts of the alkaline earth metals include $BeCO_3$, $CaCO_3$, $SrCO_3$, and the like.

The hydroxides of the alkali metals include LiOH, NaOH, KOH, RbOH, CsOH, and the like.

The hydroxides of the alkaline earth metals include $Be(OH)_2$, $Ca(OH)_2$, $Sr(OH)_2$, and the like.

The alkoxides of the alkali metals and alkaline earth metals include methoxides, ethoxides, propoxides, butoxides, phenoxides, and the like.

The amount of the metal salt is variously selected depending on the kind of the metal salt but is preferably from 0.01 to 5% by mass based on the substrates (raw materials) and, taking the reactivity and the metal salt-removing step after the reaction into consideration, it is more preferably from 0.1 to 3% by mass.

(Compound Having OH Group)

The compound (31) can be produced by reacting the compound (1) with a compound having one OH group in the presence of the metal salt and the compound (2).

The compound (32) can be produced by reacting one —$CCl_3$ group of the compound (1) with a compound having one OH group in the first-stage substitution reaction and subsequently reacting the other —$CCl_3$ group of the compound (1) with a compound having one OH group, which is different from one used in the first-stage, in a second-stage substitution reaction, in the presence of the metal salt and the compound (2).

The compound (3a) and the compound (3b) can be produced by reacting the compound (1) with a compound having two OH groups in the presence of the metal salt and the compound (2).

The branched carbonate compound can be produced by reacting the compound (1) with a compound having more than two OH groups in the presence of the metal salt and the compound (2).

The compound having one OH group is preferably, in view of usefulness of the carbonate compound obtained, at least one selected from the group consisting of methanol, ethanol, 1-propanol, 2-propanol, 1-butanol, tert-butyl alcohol, 3-oxa-1-butanol, 2,2,2-trifluoroethanol, 2,2,3,3,3-pentafluoropropanol, 2,2,3,3-tetrafluoropropanol, 1-trifluoromethyl-2,2,2-trifluoro-1-ethanol [hexafluoroisopropyl alcohol], 2,2,3,4,4,4-hexafluorobutanol, 2,2,3,3,4,4,5,5-octafluoropentanol, 2,2-difluoro-2-(1,1,2,2-tetrafluoro-2-(pentafluoroethoxy)ethoxy)ethanol [$CF_3CF_2OCF_2CF_2OCF_2CH_2OH$], 2,2-difluoro-2-(tetrafluoro-2-(tetrafluoro-2-(pentafluoroethoxy)ethoxy)ethoxy)ethanol [$CF_3CF_2OCF_2CF_2OCF_2CF_2OCF_2CH_2OH$], 2,3,3,3-tetrafluoro-2-(1,1,2,3,3,3-hexafluoro-2-(1,1,2,2,3,3,3-heptafluoropropoxy)propoxy)-1-propanol [$CF_3CF_2CF_2OCF(CF_3)CF_2OCF(CF_3)CH_2OH$], and 2,3,3,3-tetrafluoro-2-(1,1,2,2,3,3,3-heptafluoropropoxy)-1-propanol [$CF_3CF_2CF_2OCF(CF_3)CH_2OH$].

In the present invention, since the compound (2) capable of maintaining the solubility of the metal salt in the substrates even when chloroform is present in the reaction system is used, it is not necessary to remove the chloroform by distillation. Therefore, even in the case where chloroform cannot be removed by distillation since the compound having one OH group forms an azeotrope with chloroform, a carbonate compound can be produced in high yields.

Accordingly, the present invention is particularly effective in the case where the compound having one OH group is a compound that forms an azeotrope with chloroform, specifically in the case of at least one selected from the group consisting of methanol, ethanol, 1-propanol, 2-propanol, 2,2,2-trifluoroethanol, 2,2,3,3,3-pentafluoropropanol, 2,2,3,3-tetrafluoropropanol, and 1-trifluoromethyl-2,2,2-trifluoro-1-ethanol [hexafluoroisopropyl alcohol].

The compound having two OH groups is preferably, in view of usefulness of the carbonate compound obtained, at least one selected from the group consisting of ethylene glycol, 1,2-propylene glycol, 3-methyl-1,5-pentanediol, 3-oxa-1,5-pentanediol, 1,6-hexanediol, 1,3-propanediol, 1,2-butanediol, and 1,4-butanediol.

The compound having more than two OH groups includes trivalent or higher valent aliphatic alcohols and mixtures of a trivalent or higher valent aliphatic alcohol and the compound having two OH groups. In the case of the mixtures, "more than two" indicates the average number of the terminal OH groups in the compound.

The trivalent or higher valent aliphatic alcohols include, in view of versatility on industrial use, glycerin, diglycerin, polyglycerin, trimethylolpropane, 1,2,6-hexanetriol, pentaerythritol, tetramethylolcyclohexane, methylglycoside, sorbitol, mannitol, dulcitol, sucrose, and the like.

In the case of producing the compound (31), the ratio of the number of moles of the initially charged compound having one OH group to the number of moles of the initially charged compound (1) (compound having one OH group/compound (1)) is preferably more than 2, more preferably 2.5 or more, and particularly preferably 3 or more from the standpoint of improving the yields of the compound (31). When the ratio is controlled to be more than 2, the equilibrium of the reaction is shifted to the compound (31) side to improve the reaction yields. In the case of producing the compound (32), it is preferred for improving the reaction yields of the compound (32) that the reaction is carried out with controlling the ratio of the number of moles of the initially charged compound having one OH group to the number of moles of the initially charged compound (1) (compound having one OH group/compound (1)) to be 1 and thereafter the reaction is conducted with maintaining the ratio of the number of moles of another compound having one OH group to the number of moles of the initially charged compound (1) (compound having one OH group/compound (1)) to be between 1 and 1.5. When it is less than 1, the reaction cannot be completed and hence the yields decrease. When it is more than 1.5, a product in which both sides are substituted with the another compound having one OH group that is added later increases, so that the yields of the objective compound decrease.

In the case of producing the compound (3a), the ratio of the substrates, that is, the compound having two OH groups to the compound (1), is preferably from 0.1 to 10 molar equivalents and, form the standpoints of reaction efficiency and yields, more preferably from 0.5 to 2 molar equivalents.

In the case of producing the compound (3b), the ratio of the substrates varies depending on the molecular weight of the compound (3b) but the compound having two OH groups to the compound (1) is preferably from 0.5 to 2 molar equivalents and more preferably from 0.75 to 1.5 molar equivalents.

In the case of producing the branched carbonate compound, the ratio of the substrates varies depending on the molecular weight of the branched carbonate compound but the compound having more than two OH groups to the compound (1) is preferably from 0.5 to 2 molar equivalents and more preferably from 0.75 to 1.5 molar equivalents.

(Production Conditions)

In the present invention, it is preferred to carry out at least a part of the reaction of the compound (1) with the compound having an OH group at a reaction temperature of 40 to 200° C.

When the reaction is carried out at different reaction temperatures in the early stage of the reaction and in the later stage of the reaction, reaction efficiency can be improved. This is because the substitution reactions of two —$CCl_3$ group of the compound (1) proceed stepwise, and the reaction rate of the first-stage substitution reaction is high and the reaction rate of the second-stage substitution reaction is relatively low. Since the first-stage substitution reaction easily proceeds at a relatively low temperature of about 0 to 100° C. and is a reaction involving vigorous heat generation for a while, it is preferred to allow the reaction to proceed at a relatively low temperature in the early stage of the reaction. The second-stage substitution reaction is preferably carried out at a relatively high temperature of about 50 to 200° C. from the standpoint of the reaction rate.

The reaction pressure is usually atmospheric pressure. Depending on the vapor pressure of the compound having an OH group at the reaction temperature, it is preferred to apply pressure.

In the present reaction, chloroform having a low boiling temperature is formed as the reaction proceeds. Accordingly, in order to improve the reaction yields by shifting the reaction equilibrium to the carbonate compound side and to complete the reaction stoichiometrically, it is preferred to carry out the reaction with removing the formed chloroform by distillation from the reaction system.

As a method for removing chloroform by distillation, a reaction distillation mode utilizing the fact that chloroform has a low boiling point as compared with the compound having an OH group and the carbonate compound is preferred from the viewpoint of easy implementation.

On the other hand, from the standpoints that it is unnecessary to use a dedicated facility for removing chloroform by distillation and the carbonate compound and chloroform can be separated by using a usual facility for distillation for purification after completion of the reaction, it is preferred to carry out the reaction without removing the formed chloroform by distillation from the reaction system.

Incidentally, in the case where the compound having an OH group forms an azeotrope with chloroform, when the reaction is allowed to proceed while removing chloroform by distillation, the compound having an OH group used as a raw material is also removed by distillation to the outside of the reaction system together with the chloroform. In the case of reacting such a compound having an OH group, it is preferred to complete the reaction in the presence of chloroform without removing the chloroform formed in the reaction by distillation.

Furthermore, in such a case where highly pure chloroform is extracted to the outside of the reaction system and effectively utilized, it is indispensable to continue the reaction until the compound having an OH group that is used as a raw material decreases to an amount less than the compositional ratio that is the azeotropic composition with chloroform, and it is preferred to complete the reaction so as to reduce the unreacted components as far as possible.

In such a reaction system, since chloroform that is a non-polar solvent accounts for a large proportion in the reaction system as compared with the compound having an OH group, there occurs a phenomenon that the solubility of the metal salt used as a catalyst in the substrates becomes extremely low and, as a result, the reaction rate becomes very low. In such a case, the presence of the compound (2) becomes particularly important.

(Functions and Effects)

Since the process for producing a carbonate compound of the present invention as described in the above is a process of reacting the compound (1) with the compound having an OH group in the presence of the metal salt that is a catalyst to obtain a carbonate compound, a symmetrical dialkyl carbonate, an asymmetrical dialkyl carbonate, a cyclic carbonate, a polycarbonate, and the like can be selectively prepared without restraint in one reaction process by suitably changing the compound having an OH group.

Moreover, since it is a process of reacting the compound (1) with the compound having an OH group in the presence of the metal salt and the compound (2) to obtain a carbonate compound, a carbonate compound can be produced in high yields without necessity of removing chloroform as a by-product by distillation.

Furthermore, a carbonate compound can be produced without using toxic compounds such as phosgene and crown ether.

In addition, corrosive gases such as hydrogen chloride are not produced as by-products and thus it does not involve problems such as the corrosion of production facilities.

Moreover, industrially useful chloroform can be simultaneously produced.

EXAMPLES

The present invention will be explained in greater detail with reference to Inventive Examples, but the present invention should not be construed as being limited to these Inventive Examples.

Examples 1 to 5 are Inventive Examples and Examples 6 and 7 are Comparative Examples.

(Gas Chromatograph)

The analysis on a gas chromatograph (hereinafter referred to as GC) was carried out using a 6890 series manufactured by Agilent Company under the following conditions.

Column: DB-1301 (manufactured by J & W Company), 60 m,
Inner diameter: 0.25 mm,
Film thickness: 1 μm,
Column temperature: 40° C. (raised at 10° C./min) 280° C.,
Injection temperature: 300° C.,
Detector temperature: 300° C.,
Detection method: FID.

Example 1

Production Example of Dimethyl Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748), 1,024 g (32.0 mol) of methanol (Tokyo Chemical Industry Co., Ltd., M0097) and 80 g (0.36 mol) of tetraglyme (Tokyo Chemical Industry Co., Ltd., B0497), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 75° C. over a period of 2 hours while performing sufficient stirring. Chloroform formed by the reaction during the temperature elevation was refluxed by means of the Dimroth condenser fitted to the reactor. The inner temperature of the reactor was a temperature near to 55° C. that is an azeotropic temperature with the generated chloroform in the early stage of the reaction, i.e., a stage where the conversion of methanol as a raw material was low, but rose to a temperature near to 61° C. that is a boiling temperature of chloroform when the amount of remaining methanol decreased as the reaction proceeded. From the time point where the inner temperature of the reactor reached 60° C., the reaction was continued for 2 hours and then the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 5,153 g (recovery rate: 98% by mass) was collected. Upon GC analysis of the distillate fractions, it was confirmed that dimethyl carbonate was formed in 97% by mass as a yield based on hexachloroacetone.

Example 2

Production Example of Bis(2,2,3,3-tetrafluoropropyl) Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748), 4,226 g (32.0 mol) of 2,2,3,3-tetrafluoro-1-propanol (Tokyo Chemical Industry Co., Ltd., T0101) and 80 g (0.36 mol) of tetraglyme (Tokyo Chemical Industry Co., Ltd., B0497), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 70° C. over a period of 2 hours while performing sufficient stirring. Chloroform formed by the reaction during the temperature elevation was refluxed by means of the Dimroth condenser fitted to the reactor. The inner temperature of the reactor was a temperature near to 55° C. that is an azeotropic temperature with the generated chloroform in the early stage of the reaction, i.e., a stage where the conversion of 2,2,3,3-tetrafluoro-1-propanol as a raw material was low, but rose to a temperature near to 61° C. that is a boiling temperature of chloroform when the amount of remaining 2,2,3,3-tetrafluoro-1-propanol decreases as the reaction proceeded. From the time point where the inner temperature of the reactor reached 60° C., the reaction was continued for 2 hours and then the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 8,291 g (recovery rate: 98% by mass) was collected. Upon GC analysis of the distillate fractions, it was confirmed that bis(2,2,3,3-tetrafluoropropyl) carbonate was formed in 97% by mass as a yield based on hexachloroacetone.

Example 3

Production Example of Dibutyl Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748), 2,372 g (32.0 mol) of 1-butanol (Tokyo Chemical Industry Co., Ltd., B0704) and 80 g (0.36 mol) of tetraglyme (Tokyo Chemical Industry Co., Ltd., B0497), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 75° C. over a period of 2 hours while performing sufficient stirring. Chloroform formed by the reaction during the temperature elevation was refluxed by means of the Dimroth condenser fitted to the reactor. The inner temperature of the reactor rose to a temperature near to 61° C. that is a boiling temperature of the generated chloroform, from the early stage of the reaction. From the time point where the inner temperature of the reactor reached 60° C., the reaction was continued for 2 hours and then the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 6,407 g (recovery rate: 97% by mass) was collected. Upon GC analysis of the distillate fractions, it was confirmed that dibutyl carbonate was formed in 98% by mass as a yield based on hexachloroacetone.

Example 4

Production Example of Dimethyl Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748), 1,024 g (32.0 mol) of methanol (Tokyo Chemical Industry Co., Ltd., M0097) and 97 g (0.72 mol) of diglyme (Tokyo Chemical Industry Co., Ltd., B0498), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 75° C. over a period of 2 hours while performing sufficient stirring. Chloroform formed by the reaction during the temperature elevation was refluxed by means of the Dimroth condenser fitted to the reactor. The inner temperature of the reactor was a temperature near to 55° C. that is an azeotropic temperature with the generated chloroform in the early stage of the reaction, i.e., a stage where the conversion of methanol as a raw material was low, but rose to a temperature near to 61° C. that is a boiling temperature of chloroform when the amount of remaining methanol decreased as the reaction proceeded. From the time point where the inner temperature of the reactor reached 60° C., the reaction was continued for 2 hours and then the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 5,064 g (recovery rate: 96% by mass) was collected. Upon GC analysis of the distillate fractions, it was confirmed that dimethyl carbonate was formed in 95% by mass as a yield based on hexachloroacetone.

Example 5

Production Example of Dimethyl Carbonate:

Into a three-necked glass reactor having an internal volume of 10 L, which was fitted with a dropping funnel and a Dimroth condenser whose cooling section was cooled to 10° C. were charged 21 g (0.36 mol) of KF (Tokyo Chemical Industry Co., Ltd., P1758), 1,024 g (32.0 mol) of methanol (Tokyo Chemical Industry Co., Ltd., M0097) and 80 g (0.36 mol) of tetraglyme (Tokyo Chemical Industry Co., Ltd., B0497), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 75° C. over a period of 2 hours while performing sufficient stirring. Chloroform formed by the reaction during the temperature elevation was refluxed by means of the Dimroth condenser fitted to the reactor. The inner temperature of the reactor was a temperature near to 55° C. that is an azeotropic temperature with the generated chloroform in the early stage of the reaction, i.e., a stage where the conversion of methanol as a raw material was low, but rose to a temperature near to 61° C. that is a boiling temperature of chloroform when the amount of remaining methanol decreased as the reaction proceeded. From the time point where the inner temperature of the reactor reached 60° C., the reaction was continued for 2 hours and then the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 4,943 g (recovery rate: 94% by mass) was collected. Upon GC analysis of the distillate fractions, it was confirmed that dimethyl carbonate was formed in 87% by mass as a yield based on hexachloroacetone.

Example 6

Comparative Production Example of Dimethyl Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748) and 1,024 g (32.0 mol) of methanol (Tokyo Chemical Industry Co., Ltd, M0097), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 75° C. over a period of 2 hours while performing sufficient stirring. The reaction was continued for 6 hours while chloroform formed by the reaction during the temperature elevation was refluxed by means of the Dimroth condenser fitted to the reactor. The inner temperature of the reactor was a temperature near to 55° C. that is an azeotropic temperature with chloroform, during the continuation of the reaction. After the lapse of 6 hours, the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 5,153 g (recovery rate: 98% by mass) was collected. As a result of GC analysis of the distillate fractions, dimethyl carbonate was not detected at all and hexachloroacetone and methanol as raw materials and chloroform were only detected except that methyl 1,1,1-trichloroacetate was formed in 30% by mass as a yield based on hexachloroacetone.

Example 7

Comparative Production Example of Bis(2,2,3,3-tetrafluoropropyl) Carbonate:

Into a three-necked glass reactor having an internal volume of 10 L, which was fitted with a dropping funnel and a Dimroth condenser whose cooling section was cooled to 10° C. were charged 50 g (0.36 mol) of $K_2CO_3$ (Tokyo Chemical Industry Co., Ltd., P1748) and 4,226 g (32.0 mol) of 2,2,3,3-tetrafluoro-1-propanol (Tokyo Chemical Industry Co., Ltd, T0101), followed by heating to 30° C. on an oil bath. Thereafter, thereto was added dropwise the whole amount of 4,154 g (15.7 mol) of hexachloroacetone (Tokyo Chemical Industry Co., Ltd., H0335) from the dropping funnel under stirring while regulating the dropping rate so that the temperature in the reactor did not exceed 50° C. After completion of the dropwise addition, the temperature of the oil bath was gradually elevated to 70° C. over a period of 2 hours while performing sufficient stirring. The reaction was continued for 6 hours while chloroform formed by the reaction during the temperature elevation was refluxed by means of the Dimroth condenser fitted to the reactor. The inner temperature of the reactor was a temperature near to 55° C. that is an azeotropic temperature with chloroform, during the continuation of the reaction. After the lapse of 6 hours, the reaction was terminated by lowering the temperature. After completion of the reaction, the Dimroth condenser fitted to the upper part was replaced with a distillation line cooled to 10° C. Then, the pressure in the reactor was gradually lowered via a pressure control valve fitted to the distillation line side by means of a vacuum pump and the inner temperature of the reactor was gradually elevated while continuing the pressure reduction until it finally reached 20 mmHg. While collecting distillate fractions, the distillation was continued until no liquid was finally present in the reactor, thereby collecting the whole amount of the reaction product.

As the distillate fractions, 8,291 g (recovery rate: 98% by mass) was collected. As a result of GC analysis of the distillate fractions, bis(2,2,3,3-tetrafluoropropyl) carbonate was not detected at all and hexachloroacetone and 2,2,3,3-tetrafluoro-1-propanol as raw materials and chloroform were only detected except that $CCl_3COOCH_2CF_2CHF_2$ was formed in 40% by mass as a yield based on hexachloroacetone.

While the invention has been described in detail and with reference to specific embodiments thereof, it will be apparent to one skilled in the art that various changes and modifications can be made therein without departing from the spirit and scope thereof.

INDUSTRIAL APPLICABILITY

The dialkyl carbonates obtained by the production process of the present invention can be applied to various uses and are useful as organic solvents, resin raw materials, raw materials for pharmaceuticals and agricultural chemicals, and the like.

The cyclic carbonates obtained by the production process of the present invention are industrially extremely useful as solvent applicable to various uses, electrolytes, resist removers, acrylic fiber processors, hydroxyethylating agents, raw materials for pharmaceuticals, soil hardeners, and the like.

The polycarbonates obtained by the production process of the present invention are useful, as oligomers having a reactive OH group in the terminal, as raw materials for various polymer materials such as highly functional polyurethanes, polyesters, polycarbonates, and epoxy resins, reactive diluents, reactive plasticizers, and the like.

The invention claimed is:

1. A method for producing a carbonate compound, comprising reacting a compound represented by the following formula (1) with a compound having an OH group in the presence of a metal salt and 0.2 to 4.0 mol of a compound represented by the following formula (2) per mol of the metal salt to obtain a compound having a carbonate bond,

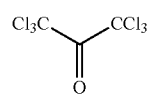 (1)

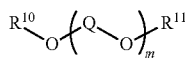 (2)

wherein
m is an integer of from 1 to 10,
Q is an alkylene group having 1 to 4 carbon atoms or a group in which one or more hydrogen atoms of the alkylene group are replaced by an alkyl group having 1 to 5 carbon atoms or by an alkyl group having 2 to 5 carbon atoms and having an ethereal oxygen atom between carbon atom-carbon atom, and Q in the case where m is 2 or more may be the same group or a different group, and
$R^{10}$ and $R^{11}$ are each independently an alkyl group having 1 to 5 carbon atoms,
wherein, during the reaction of the compound represented by the formula (1) with the compound having an OH group, chloroform produced by the reaction is not removed by distillation.

2. The method for producing a carbonate compound according to claim 1, wherein the metal salt is at least one kind selected from the group consisting of salts of alkali metals and salts of alkaline earth metals.

3. The method for producing a carbonate compound according to claim 1, wherein the compound represented by the above formula (2) is a compound represented by the following formula (21):

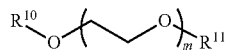 (21)

wherein
m is an integer from 2 to 6 and
$R^{10}$ and $R^{11}$ are each independently an alkyl group having 1 to 5 carbon atoms.

4. The method for producing a carbonate compound according to claim 1, wherein the compound having a carbonate bond is a compound represented by the following formula (31) or a compound represented by the following formula (32):

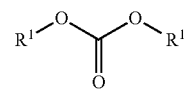 (31)

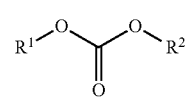 (32)

wherein
$R^1$ and $R^2$ represent each a monovalent aliphatic hydrocarbon group and $R^1$ and $R^2$ are not the same group.

5. The method for producing a carbonate compound according to claim 1, wherein the compound having a carbonate bond is a cyclic carbonate compound represented by the following formula (3a):

 (3a)

wherein
$R^3$ represents a divalent aliphatic hydrocarbon group.

6. The method for producing a carbonate compound according to claim 1, wherein the compound having a carbonate bond is a chainlike carbonate compound represented by the following formula (3b):

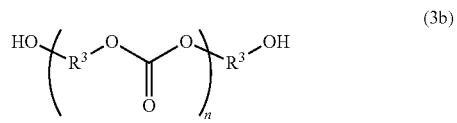 (3b)

wherein
$R^3$ represents a divalent aliphatic hydrocarbon group and n represents an integer of from 1 to 1,000.

7. The method for producing a carbonate compound according to claim 1, wherein the compound having an OH group is at least one selected from the group consisting of methanol, ethanol, 1-propanol, 2-propanol, 1-butanol, tert-butyl alcohol, 3-oxa-1-butanol, 2,2,2-trifluoroethanol, 2,2,3,3,3-pentafluoropropanol, 2,2,3,3-tetrafluoropropanol, 1-trifluoromethyl-2,2,2-trifluoro-l-ethanol, 2,2,3,4,4,4-hexafluorobutanol, 2,2,3,3,4,4,5,5-octafluoropentanol, 2,2-difluoro-2-(1,1,2,2-tetrafluoro-2-(pentafluoroethoxy)ethoxy)ethanol, 2,2-difluoro-2-tetrafluoro-2-(tetrafluoro-2-(pentafluoroethoxy)ethoxy)ethoxy)ethanol, 2,3,3,3-tetrafluoro-2-(1,1,2,3,3,3-hexafluoro-2-(1,1,2,2,3,3,3-heptafluoropropoxy)propoxy)-1-propanol, and 2,3,3,3-tetrafluoro-2-(1,1,2,2,3,3,3-heptafluoropropoxy)-1-propanol.

8. The method for producing a carbonate compound according to claim 7, wherein the compound having an OH group is at least one kind selected from the group consisting of methanol, ethanol, 1-propanol, 2-propanol, 2,2,2-trifluoroethanol, 2,2,3,3,3-pentafluoropropanol, 2,2,3,3-tetrafluoropropanol, and 1-trifluoromethyl-2,2,2-trifluoro-1-ethanol.

9. The method for producing a carbonate compound according to claim 1, wherein the compound having an OH group is at least one kind selected from the group consisting of ethylene glycol, 1,2-propylene glycol, 3-methyl-1,5-pentanediol, 3-oxa-1,5-pentanediol, 1,6-hexanediol, 1,3-propanediol, 1,2-butanediol, and 1,4-butanediol.

* * * * *